United States Patent
Trotta

Patent Number: 5,913,861
Date of Patent: *Jun. 22, 1999

[54] METHOD OF CATHETER BALLOON MANUFACTURE AND USE

[76] Inventor: Thomas N. Trotta, 218 Poinicana Island Dr., Miami, Fla. 33160

[ * ] Notice: This patent is subject to a terminal disclaimer.

[21] Appl. No.: 09/014,225

[22] Filed: Jan. 27, 1998

Related U.S. Application Data

[62] Division of application No. 08/795,248, Feb. 10, 1997, Pat. No. 5,728,104, which is a division of application No. 08/614,399, Mar. 12, 1996, Pat. No. 5,643,279.

[51] Int. Cl.[6] .................................................. A61F 11/00
[52] U.S. Cl. .............................................. 606/108; 604/96
[58] Field of Search .................................. 606/108, 194, 606/192, 198; 604/96, 103

[56] References Cited

U.S. PATENT DOCUMENTS

| | | |
|---|---|---|
| 5,156,612 | 10/1992 | Pinchuk et al. . |
| 5,449,371 | 9/1995 | Pinchuk et al. . |
| 5,490,838 | 2/1996 | Miller . |
| 5,569,296 | 10/1996 | Mavin et al. . |
| 5,609,605 | 3/1997 | Marshall et al. . |
| 5,645,560 | 7/1997 | Brocker et al. . |
| 5,674,192 | 10/1997 | Schatjian et al. .......................... 604/96 |
| 5,766,201 | 6/1998 | Ravenscroft et al. ................... 606/108 |

*Primary Examiner*—Michael Buiz
*Assistant Examiner*—Kevin Truong
*Attorney, Agent, or Firm*—Gerstman, Ellis & McMillin, Ltd.

[57] ABSTRACT

A catheter balloon is manufactured and prepared for use by heating a portion of a thermoplastic tube and pressurizing the lumen of the tube to cause the heated tube portion to stretch. Preferably, a central section of the tube portion is heated to a degree greater than the end sections of the tube portions, so that the central section of the tube portion expands to a thinner wall thickness than the end sections of the tube portion. Thus, when this newly formed, integral balloon is expanded within a patient, the central section thereof tends to expand outwardly first, ahead of the end sections. When such a balloon carries a tubular stent within the patient, the early expansion of the central section against a longitudinally centered stent causes a central portion of the stent to expand outwardly first, keeping the stent firmly centered on the balloon as it is expanded by the balloon.

24 Claims, 1 Drawing Sheet

METHOD OF CATHETER BALLOON MANUFACTURE AND USE

CROSS REFERENCE TO RELATED APPLICATIONS

This is a division of application Ser. No. 08/795,248, filed Feb. 10, 1997 now and U.S. Pat. No. 5,728,104 , which, in turn, is a division of application Serial No. 08/614,399, filed Mar. 12, 1996, now U.S. Pat. No. 5,643,279.

BACKGROUND OF THE INVENTION

In Miller U.S. Pat. No. 5,490,838 entitled of "Method of Inserting a Balloon Catheter", a balloon catheter is disclosed in which the balloon in its non-inflated configuration has a smooth, cylindrical wall, and is no greater in diameter than the remainder of the catheter. The balloon, in its original form, is a tube made of an elastically expandable, work-hardenable plastic, such as known forms of nylon or polyethylene (polyethylene terephalate).

A stated advantage of such a balloon lies on the fact that as the balloon expands with increasing internal pressure, there is a pressure range which the work-hardening primarily takes place which has an effect of reducing or eliminating the expansion of the balloon with increasing pressure. Thus, if a doctor expands the balloon within a patient to this pressure range, he or she can know with confidence that the balloon diameter is no greater than a predetermined maximum diameter, without the need for a direct observation.

Furthermore, a popular surgical procedure for preventing restenosis in arteries utilizes a catheter dilatation balloon which is surrounded by an expandable tubular stent, for example a wire stent, or an apertured tube stent of the type sold by the Johnson and Johnson Corporation. The balloon and stent are positioned as desired within an artery or other vessel lumen of a patient. Then the balloon is expanded, to expand the stent to a desired configuration. It is desirable to avoid overexpansion from such a balloon as the stent is being expanded.

Conventional arterial dilatation balloons are flexible but not very stretchable, so that they are initially wrapped up in a folded configuration. Disadvantage has been encountered when these balloons are used with stents because of the possibility that, due to nonuniformities in the unfolding, certain portions of the stent become more greatly outwardly pressurized than other portions.

Also, if a stent balloon tends to expand one end or the other first, rather than first in the middle while in the process of expanding the stent, the stent can be driven off the balloon by such asymmetric expansion, so that the stent becomes only partially expanded. This of course can be a great problem during surgery, and may result in the stent becoming positioned improperly in the expanded configuration.

In accordance with this invention, a catheter balloon is provided which can be very narrow prior to inflation, and which can inflate in a circumferentially uniform manner, which is predictably dependent on the inflation pressure, for optimum implantation of stents within the body, and also for other medical uses which are customary for catheter balloons.

DESCRIPTION OF THE INVENTION

In accordance with this invention, a method is provided for preparing a catheter balloon for inflation and for inflating the balloon, which comprises:

(A) A portion of a stretchable tube capable of undergoing molecular orientation is radially stretched until said radially stretched tube portion exhibits a desired increase in molecular orientation. The term "stretchable" or "stretched" as used herein implies that the tube tends to not shrink back to its original configuration after such stretching, but it spontaneously remains substantially in its stretched configuration, apart from special measures such as heating to activate plastic memory or the like.

(B) At least part of the above tube portion is longitudinally stretched to create a desired increase in molecular orientation longitudinally relative to the tube, and to reduce the initial balloon diameter.

(C) Thereafter, the tube portion is inserted as part of a catheter into a patient, for example, into a coronary artery. A lumen of the tube portion is pressurized to cause radial expansion of the tube portion within the patient, for advantages as described in the cited Miller patent, and also as described below.

Further in accordance with this invention, a balloon may be made from thermoplastic tube by radially stretching at least a portion of the thermoplastic tube in step (A) while causing a central section of the tube portion to stretch to a lesser wall thickness than end sections of the tube portion. Preferably, one then longitudinally stretches at least part of the tube portion to reduce the diameter of the catheter balloon prepared from the thermoplastic tube prior to inflation. Also, when the thermoplastic used can be significantly oriented on a molecular basis, the balloon can be biaxially oriented by the radial stretching step and the longitudinal stretching step. This characteristic of many plastics is a well-known and understood property.

Thereafter one can insert the tube portion as part of a catheter into a patient, pressurizing the lumen of the tube by an amount sufficient to cause radial expansion of the tube portion to take place within the patient while the tube portion is surrounded by an expansible stent for implantation. Because, by this invention, a central section of the tube portion may be of lesser wall thickness than end sections of the same tube portion, at least initially more radial expansion of the central section of the tube portion takes place than at end sections thereof. Thus, a central portion of the stent can be expanded first within the patient, with the entire stent being subsequently expanded by further inflation of the balloon formed from the tube portion, to provide spontaneous assurance that the stent will not shift on the balloon during the inflation of the balloon and expansion of the stent. The balloon's radial expansion tends to begin in the middle, and spreads to the ends. Thus, a surrounding, centered stent is not pushed off of the balloon, as may be the case if the balloon expands at one end first.

Also, as described in the previously cited patent application, the balloon's radial expansion may cause molecular orientation of the tube portion, resulting in work-hardening, so that, at a predetermined pressure range, the diameter of the balloon formed from the tube portion is relatively constant and known.

If desired, prior to step A above, at least some of the plastic tube portion may be longitudinally stretched to create increased longitudinal molecular orientation. The details of this and the above stretching steps may be performed as described in Pinchuk et al. U.S. Pat. No. 5,156,612, with the exception of that, contrary to the teachings of that patent, the final balloon inflation step disclosed therein takes place within the patient, and not as a process step in the manufacturing of the balloon and catheter.

Numerous, different plastic formulations undergo molecular orientation, so as to be useable to manufacture plastic tubes for processing in accordance with this invention. Specifically, the balloon-forming plastic tube may be made of stretchable forms of nylon and polyethylene polymers or copolymers (such as poly (ethylene-propylene) which exhibit desired properties for use herein. Specifically nylons 612, 11, and 12 may be used, typically of an intrinsic viscosity of about 1.6 to 2.2 as determined by The International Standards Organization Test ISO 307/DIN 53 727, with m-creosol as a solvent, employing a concentration of 0.5 gm. of nylon 12 per 100 ml. of M-creosol. With nylon 12, an intrinsic viscosity of about 2.1 is preferred.

The tube portion which is to be inserted into the patient preferably has a diameter prior to said pressurizing of step (C) above within the patient of no more than about twice the minimum diameter of adjacent tubing of the catheter. Preferably, the pre-expanded tube portion discussed above may have a diameter of less than 50 percent over the minimum diameter of adjacent catheter tubing, and is preferably of substantially equal diameter to such catheter tubing, so that the tube portion which is to become the balloon may slide easily along with the rest of the catheter tubing into a nonexpanded, tubular stent, and into a blood vessel or body lumen without difficulty.

Also, the formed balloon preferably has an outer wall that is smooth and free of folds, contrary to the presently conventional catheter dilatation balloons for angioplasty and the like. This is rendered possible by the stretching capability of the catheter tube portion to form the desired balloon, while at the same time one or more desired maximum balloon expansion diameters (one larger than the other) may optionally be achieved at predetermined pressure ranges in the manner described in the cited Miller patent application.

It is also preferred for the length of the plastic portion which is radially stretched in step (A) above to be less than and included in the length of the plastic portion which is longitudinally stretched in step (B). The stent, when applied to the balloon described herein, may be preferably longitudinally centered on the length of the plastic portion which is radially stretched. As described above, a central portion of the balloon of this invention preferably tends to expand first, causing a central portion of the stent to expand first relative to end portions thereof. Then, the end parts of the plastic tube portion longitudinally stretched will expand also, to cause end portions of the stent to expand as well. However, by this technique the stent will not slide off the balloon, avoiding the problem which has been encountered in some surgical procedures.

Other orientable thermoplastic materials may be used as well as nylon and polyethylene as orientable thermoplastics for use as a catheter balloon in accordance with this invention. They may be selected from other materials such as polyimide block copolymers, polyamide copolymers, amorphous polyamides, and polyester copolymers, for example.

In each of steps (A) and (B) above, the molecular orientation of the tube is accomplished by applying a force greater than the material's yield point to cause stretching, but less that its ultimate tensile strength. In the radial expansion or stretching step (A), control of the location of the material which is stretched may be made by the local application of heat, to lower the yield point of the desired area where radial expansion is to be achieved. A gradation of heat applied can cause the middle of the newly-formed balloon to stretch more than end portions and thus to have a lower wall thickness. Alternatively the tube may initially have a thinner central portion.

The tubing section may be re-oriented sequentially by longitudinal stretching, followed by radial pressurized stretching, without a significant loss of shape-forming capability. It may be desirable in some cases to sequentially repeat the respective steps (A) and (B) several times, as may be desired.

DESCRIPTION OF SPECIFIC EMBODIMENTS

Figure 1:
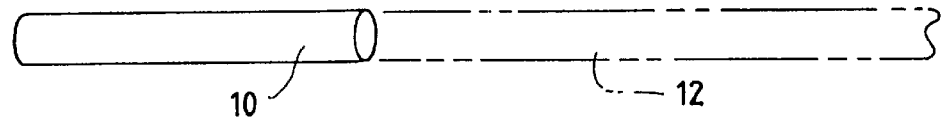
FIG. 1 is a perspective view of a portion of a plastic tube, or if desired, an entire length of tube, which is to be biaxially oriented in accordance with this invention for the formation of a catheter balloon.

Referring to the drawings, a method for preparing a catheter balloon for inflation and for inflating the balloon is illustrated. A plastic tube 10 is provided in accordance with FIG. 1, the plastic material of the tube preferably having the capability to undergo biaxial orientation. For example, a relatively low crystalline nylon 12 may be used to manufacture tube 10.

Tube 10 may be either bonded to a catheter tube 12 during the manufacturing steps of the method of this invention, or subsequently, prior to use of expanding the balloon within the patient. Alternatively, tube 10 may be integrally extruded with catheter tube 12.

Figure 2:
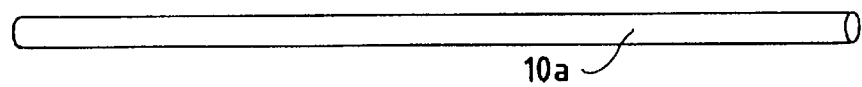
FIG. 2 is a perspective view of the tube portion of FIG. 1 after it has been longitudinally stretched in accordance with a preferred embodiment of this invention.

As a first preferred step, especially for use with nylons 612, 11 or 12, tube 10 is longitudinally stretched as in FIG. 2 to create a desired, increased, longitudinal molecular orientation relative to the tube, as illustrated by tube boa, which comprises the stretched portion of tube 10 after the first step of processing. Specific conditions for this processing may vary, depending upon the materials, but are generally familiar to those skilled in the art of the molecular orientation of plastics. Also, the pertinent disclosures of Pinchuk et al. U.S. Pat. No. 5,156,612 may be utilized in developing a specific process, the disclosures of that patent being incorporated by reference herein.

Figure 3:
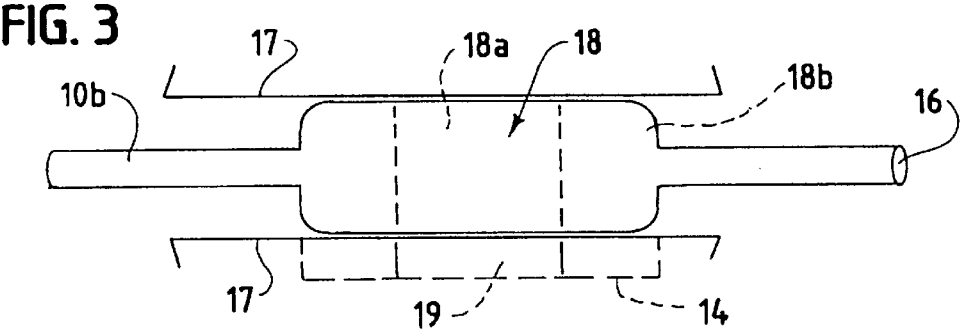
FIG. 3 is a perspective view of the plastic tube portion of FIG. 2 after a smaller portion thereof has been radially stretched in accordance with step (A) as described above.

FIG. 3 corresponds to method step (A) above, as previously discussed. Tubing 10 a from FIG. 2 may have a portion thereof heated by a conventional heater 14, so that the yield point of the heated plastic drops relative to the remaining plastic of tube 10b, which is tube 10a as modified by the processing step of FIG. 3. Then, lumen 16 of the tube may be pressurized in a mold 17 to restrict balloon expansion and to cause a preliminary balloon 18 to form. A desired, increased radial expansion and molecular orientation is provided to balloon 18, resulting in at least a degree of biaxial orientation to balloon 18.

Heater 14 may have a central section 19 that heats a central portion 18a of balloon 18 slightly more than the terminal portions 18b of the balloon. Thus, the wall thickness of balloon 18a may be slightly reduced relative to the wall thickness of balloon end portions 18b. Mold 17 may have an appropriate outward bulge if desired to accommodate the added stretching and thinning of the walls of central section 18a. For example, the wall thickness of central catheter balloon portion 18a may be approximately 0.0003 to 0.0015 inch while the wall thicknesses of end portions 18b may be approximately 0.0002 inch thicker than the wall thickness of portion 18a after the expansion of FIG. 3 and prior to the processing of FIG. 4.

Figure 4:
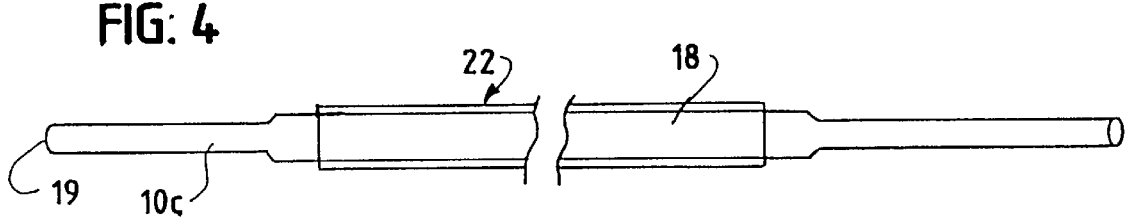
FIG. 4 is a perspective view of the tube of FIG. 3 after it has been again longitudinally stretched in accordance with step (B) as described above, and showing a stent placed thereon for purposes of illustration.

Thereafter, the step of FIG. 4 may preferably be performed, which is step (B) as previously described, in which tube portion 10 *b* is longitudinally stretched to form tube portion 10c as shown in FIG. 4. Balloon 18 exhibits a reduction in diameter, with the prior internal pressurizing within the tube being released to facilitate the desired longitudinal stretching, for further longitudinal molecular orientation of the plastic tube. Preferably, the balloon formed has an equal diameter at its opposed ends.

Then, contrary to the cited Pinchuk et al. patent, the catheter is ready for medical use except for the known and necessary steps such as sterilization, adding components, and the like. Catheter portion 10c may be attached to the rest of the catheter if that has not been previously done.

Figure 5:
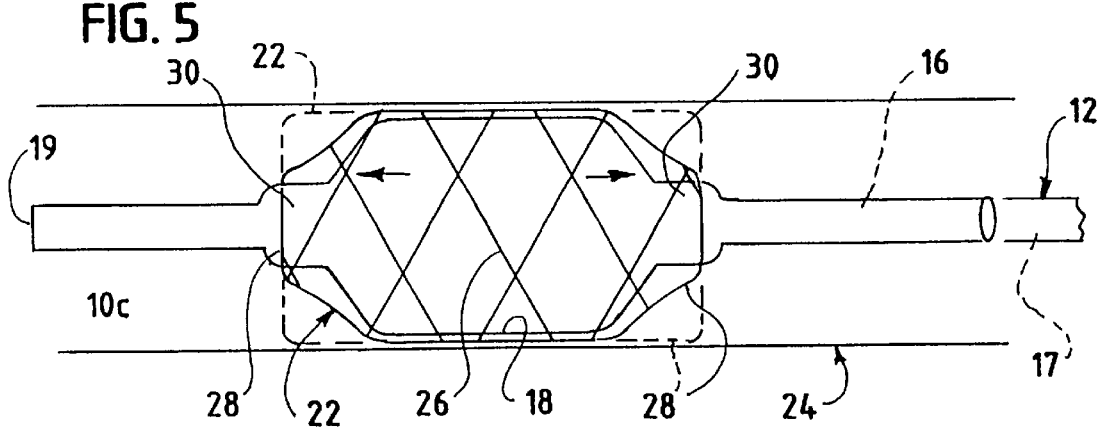
FIG. 5 is a fragmentary, perspective view of a catheter which incorporates the plastic tube balloon of this invention, which is attached onto the end of the catheter and inserted into a coronary artery, schematically showing the stent surrounding the balloon after partial inflation thereof, where a central portion of the stent and balloon are inflated more than end portions thereof.

Referring to FIG. 5, catheter 12 is shown carrying plastic tube portion 10c. Lumen 16 communicates with an inflation lumen 17 of the rest of catheter 12. Tube portion has a closed, distal end 19 in this embodiment. However, if desired, multiple lumen catheters may be provided in which at least one lumen passes through end 19 while the inflation lumen terminates in the area of balloon 18.

Balloon 18 carries a tubular, crossing-wire, or aperturedtube, expansible stent 22 of conventional design, with the catheter 12 and stent 22 being shown to be occupying an artery 24 of a patient. Stent 22 is placed about plastic tube portion 10c while in the collapsed configuration of FIG. 4. Then, when balloon 18 and stent 22 have been positioned at the proper place in artery 24, the lumen of catheter 10c is inflated to a predetermined pressure. Balloon 18 expands as shown in FIG. 5, with the middle of balloon portion 18 being centrally located within stent 22. The center of balloon 18 expands first, since it is of slightly reduced wall thickness, expanding a central portion 26 of stent 22 outwardly more rapidly than the expansion of the end portions 28 of the stent. This causes the stent to remain in position on the balloon, and not to be forced off the balloon by its expansion, as may take place when expansion begins at an end portion of the stent. Following this, end portions 30 of the balloon may be inflated more than shown, to drive added portions of the stent 22 radially outwardly into a fully expanded configuration, as shown in dotted lines.

Following the desired expansion of the stent, the lumen of tubing 10c can be depressurized, causing balloon 18 to collapse, so that catheter 20 and its distal tube section 10c may be withdrawn, leaving the expanded stent 22 behind in the artery.

Because of the absence of folds in the balloon, which expands as a tube in a stretching manner with a thinning sidewall, the stent may be expanded with more uniform circumferential pressures against all of its inner surfaces (disregarding the issue of central preexpansion of the balloon). This results in better stent placement than can often be achieved with catheter balloons of the prior art. Also, balloon 18 can cease its expansion at a predetermined diameter in a predetermined elevated pressure range due to work hardening, which increases the assurance that the balloon will not be over inflated.

The above has been offered for illustrative purposes only, and is not intended to limit the scope of the invention of this application, which is as defined in the claims below.

That which is claimed:

1. The method of preparing a catheter balloon for inflation, which comprises:

heat softening a portion of a thermoplastic tube by applying a higher degree of heat to a central section of said plastic tube portion than to outer sections of said tube portion, and pressurizing a lumen of said tube portion to cause radial expansion of said heated tube portion to stretch said central section of the tube portion to a lesser wall thickness than outer sections of said tube portion.

2. The method of claim 1 which said tube portion, after said heating and stretching, has an outer wall that is smooth and free of folds.

3. The method of claim 1 in which at least some of said plastic tube portion is longitudinally stretched to create increased longitudinal molecular orientation.

4. The method of claim 3 in which the length of the plastic portion that is heated and radially stretched is less than and included in the length of plastic portion that is longitudinally stretched.

5. The method of claim 1 in which said thermoplastic tube comprises a formulation selected from the group consisting of nylon and polyethylene.

6. The method of claim 1 in which said thermoplastic tube portion that is heated and radially stretched is thereafter surrounded by an expansible stent for implantation within a patient, said stent being longitudinally centered on said plastic tube portion, whereby, upon inflation of said plastic portion, the thinner-walled central section expands first, to keep the stent centered on the plastic portion as the entire plastic portion expands, to expand the stent within said patient.

7. The method of claim 1 in which said tube portion, as part of a catheter, is inserted into a patient, and in which the tube portion lumen is pressurized within the patient to expand said tube portion in the manner of a catheter balloon, whereby a central section of the tube portion is radially expanded, at least initially, to a greater degree than outer sections of said tube portion.

8. The method of claim 7 in which said tube portion is pressurized within the patient by an amount sufficient to cause work-hardening of said tube portion to take place.

9. The method of claim 8 in which said tube portion is inserted into the patient and expanded therein while an expansible stent surrounds said tube portion in a position longitudinally centered on said tube portion, whereby the expansion of said central section of the tube portion serves to keep the stent in such centered position during expansion of the tube portion, and said stent is expanded by said expanding tube portion.

10. The method of preparing a catheter balloon for inflation and for inflating said balloon, which comprises:

heat softening a portion of a thermoplastic tube by applying a higher grade of heat to a central section of said plastic tube portion than to outer sections of said tube portion, and pressurizing a lumen of said tube portion to cause radial expansion of said heated tube portion to stretch said central section of the tube portion to a lesser wall thickness than outer sections of said tube portion, whereby, after said heating and stretching, said tube portion has an outer wall that is smooth and free of folds, and in which said tube portion is surrounded by an expansible stent for implantation within a patient, said stent being longitudinally centered on said plastic tube portion, whereby, upon inflation of said plastic portion, the thinner-walled central section expands first, to keep the stent centered on the plastic portion as the entire plastic portion expands, to expand the stent within the patient.

11. The method of claim 10 in which said tube portion carrying said stent is inserted into a patient, and in which the tube portion lumens is pressurized within the patient to expand said tube portion in the manner of a catheter balloon, whereby a central section of the tube portion is radially expanded at least initially to a greater degree than outer sections of said tube portion, and a central section of said stent is radially expanded, at least initially, to a greater degree than outer sections of said stent.

12. The method of claim 11 in which said tube portion is pressurized within the patient by an amount sufficient to cause work-hardening of said tube portion to take place.

13. The method of claim 12 in which, prior to insertion into the patient, at least some of said plastic tube portion is longitudinally stretched to create increased longitudinal molecular orientation.

14. The method of claim 13 in which the length of the plastic portion that is heated and radially stretched is less than and included in the length of plastic portion that is longitudinally stretched.

15. The method of claim 14 in which said thermoplastic tube comprises a formulation selected from the group consisting of nylon and polyethylene.

16. The method of preparing a catheter balloon for inflation, which comprises:

radially stretching at least a portion of a thermoplastic tube while causing a central section of the tube portion to stretch radially outwardly to a lesser wall thickness than end sections of the tube portion, whereby, upon inflation within a patient as a catheter balloon, a central portion of the balloon tends to expand outwardly first.

17. The method of claim 16 in which said thermoplastic tube portion is thereafter surrounded by an expansible stent for implantation within a patient, said stent being longitudinally centered on said plastic tube portion, whereby, upon inflation of said plastic portion, the thinner-walled central section expands first to keep the stent centered on the plastic portion as the entire plastic portion expands, to expand the stent within said patient.

18. The method of claim 16 in which said tube portion, after said radial stretching, has an outer wall that is smooth and free of folds.

19. The method of claim 16 in which at least some of said plastic tube portion is longitudinally stretched to create increased longitudinal molecular orientation.

20. The method of claim 19 in which the length of the plastic portion that is radially outwardly stretched is less than and included in the length of plastic portion that is longitudinally stretched.

21. The method of claim 16 in which said thermoplastic tube comprises a formulation selected from the group consisting of nylon and polyethylene.

22. The method of claim 16 in which said tube portion, as part of a catheter, is inserted into a patient, and in which the tube portion lumen is pressurized within the patient to expand said tube portion in the manner of a catheter balloon, whereby a central section of the tube portion is radially expanded, at least initially, to a greater degree than outer sections of said tube portion.

23. The method of claim 22 in which a stent is longitudinally centered on said tube portion as the tube portion and stent are inserted into a patient, whereby a central portion of said stent is radially expanded, at least initially, to a greater degree than outer sections of the stent portion as said tube portion is radially expanded.

24. The method of claim 22 in which said tube portion is pressurized with in the patient by an amount sufficient to cause work-hardening of said tube portion to take place.

\* \* \* \* \*

UNITED STATES PATENT AND TRADEMARK OFFICE
CERTIFICATE OF CORRECTION

PATENT NO. : 5,913,861
DATED : June 22, 1999
INVENTOR(S) : Thomas N. Trotta

It is certified that error appears in the above-identified patent and that said Letters Patent is hereby corrected as shown below:

Title page,
Please insert:
-- "[73] Assignee: Cordis Corporation,
   Miami Lakes, Florida " --

Signed and Sealed this

Twentieth Day of November, 2001

*Attest:*

*Attesting Officer*

NICHOLAS P. GODICI
*Acting Director of the United States Patent and Trademark Office*